(12) United States Patent
Amano et al.

(10) Patent No.: US 6,217,523 B1
(45) Date of Patent: Apr. 17, 2001

(54) BLOOD PULSE WAVE DETECTING APPARATUS AND MOTION INTENSITY MEASURING APPARATUS

(75) Inventors: Kazuhiko Amano; Motomu Hayakawa; Koji Kitazawa, all of Suwa (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 09/448,622

(22) Filed: Nov. 23, 1999

Related U.S. Application Data

(62) Division of application No. 08/808,523, filed on Feb. 28, 1997, now Pat. No. 6,022,321, which is a continuation of application No. 08/309,386, filed on Sep. 20, 1994, now abandoned.

(30) Foreign Application Priority Data

Sep. 28, 1993 (JP) ...................................... 5-241731

(51) Int. Cl.⁷ ...................................................... A61B 5/02
(52) U.S. Cl. ............................ 600/500; 600/483; 600/310
(58) Field of Search ............................ 600/485, 500–501, 600/310, 322, 481, 483

(56) References Cited

U.S. PATENT DOCUMENTS

| | | |
|---|---|---|
| 4,788,982 | 12/1988 | Gedeon et al. . |
| 4,911,427 | 3/1990 | Matsumoto et al. . |
| 4,934,372 | 6/1990 | Corenman et al. . |
| 4,951,679 | 8/1990 | Harada . |
| 4,955,379 | 9/1990 | Hall . |
| 5,101,828 | 4/1992 | Welkowitz et al. . |
| 6,022,321 | * 2/2000 | Amano et al. .................. 600/500 |

FOREIGN PATENT DOCUMENTS

| | | |
|---|---|---|
| 31 50 925 | 6/1983 | (DE) . |
| 40 01 574 | 7/1991 | (DE) . |
| 0 379 140 | 7/1990 | (EP) . |
| 0 410 658 | 1/1991 | (EP) . |
| 63-34731 | 2/1988 | (JP) . |
| 2-44534 | 10/1990 | (JP) . |

* cited by examiner

*Primary Examiner*—Max Hindenburg
*Assistant Examiner*—Ryan Carter
(74) *Attorney, Agent, or Firm*—Michael T. Gabrik

(57) ABSTRACT

An apparatus for detecting pulse waves and motion intensity of a living body in motion is disclosed. The apparatus has photosensors of the photo-coupler type for wavelengths of 660 nm and 940 nm, respectively. The sensors are attached to a person under examination, and provide output signals which include a blood pulse signal as well as body motion components superimposed on the blood pulse signal. These signals are subjected to the Fourier transformation in a fast Fourier transformation circuit, and then applied to a comparator which in turn compares amplitudes of major frequency components (components associated with pulse waves and body motion) to one another. According to the comparison result, a decision circuit discriminates the pulse wave from the body motion. A display unit displays the pulse rate corresponding to the fundamental frequency of the detected pulse wave. The display unit also displays the change in motion intensity detected by the decision circuit. Thus, the present invention allows the detection of the change in motion intensity during the exercise of a person under the examination.

8 Claims, 7 Drawing Sheets

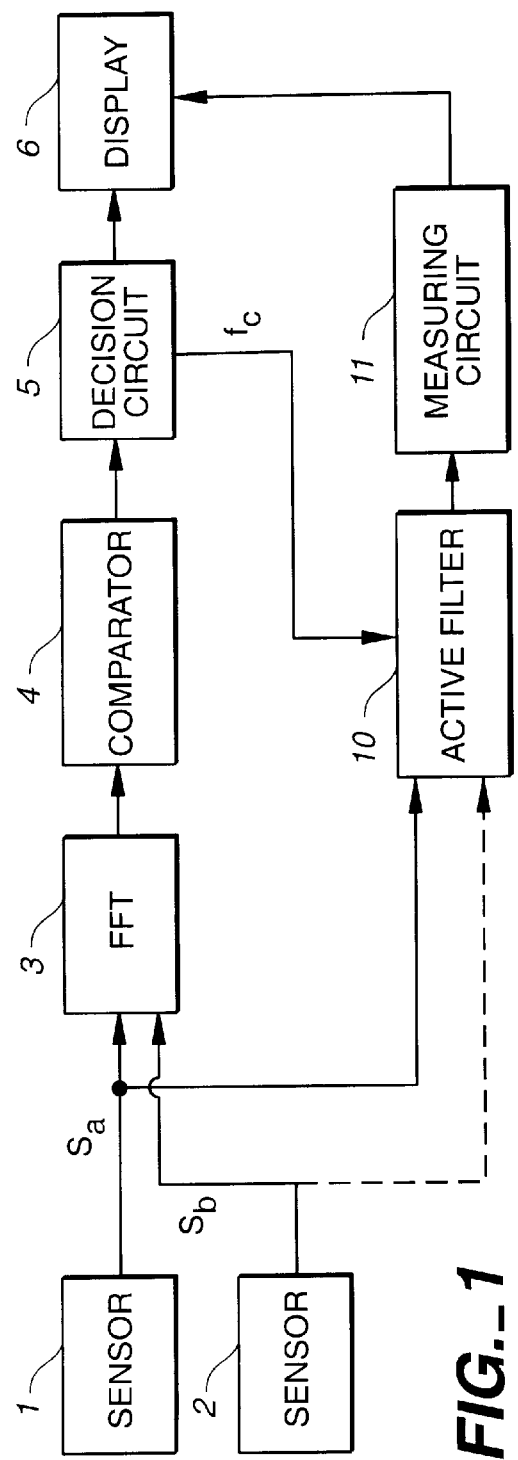

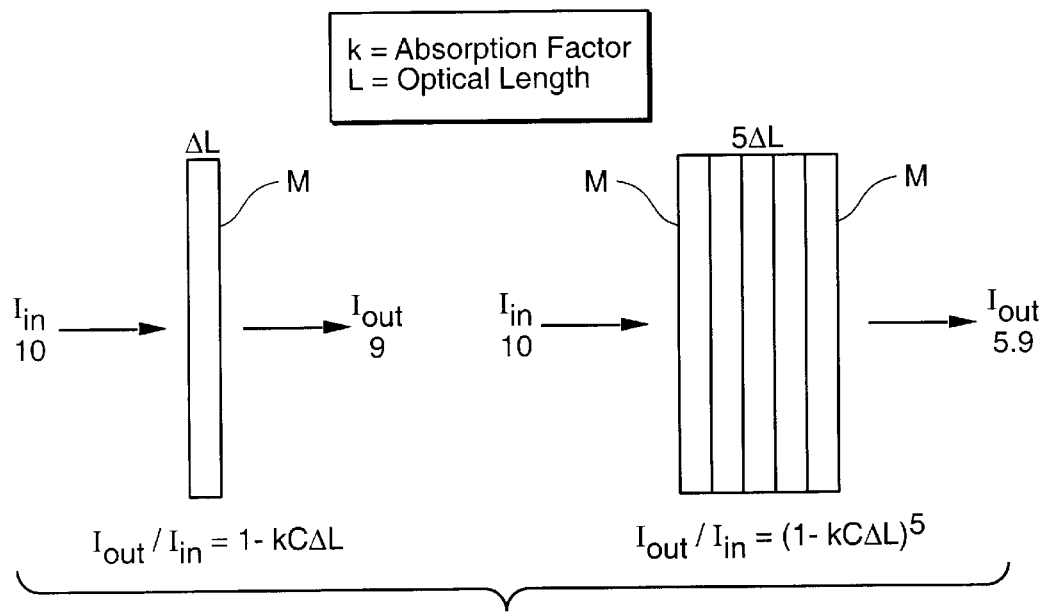
FIG._3
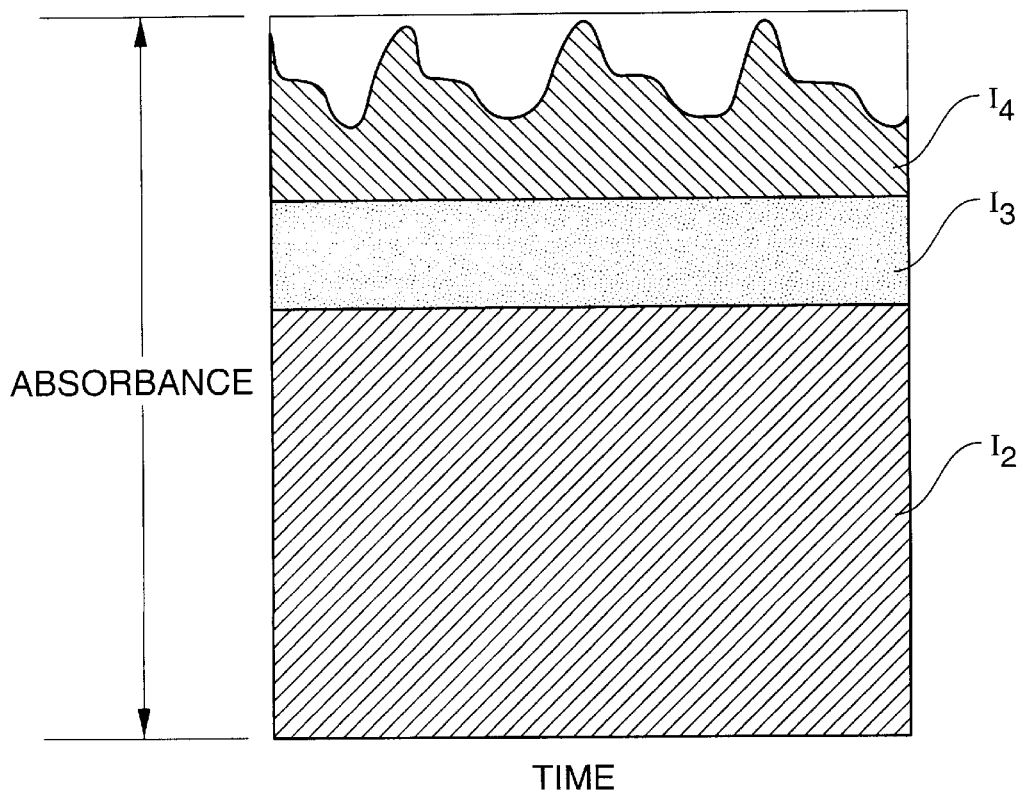
FIG._4

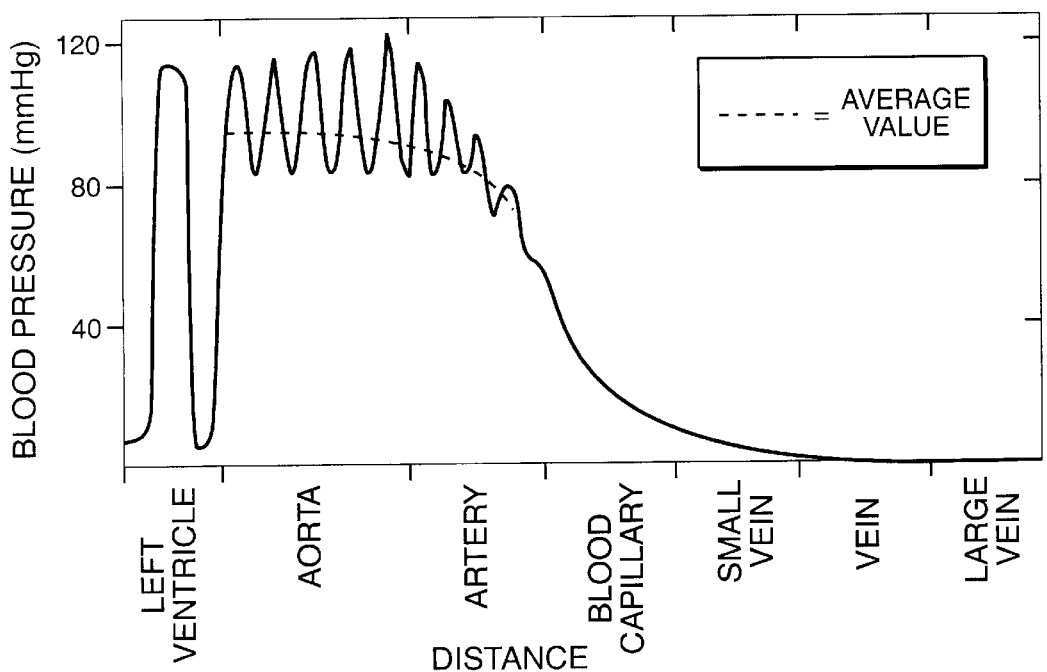
FIG._5
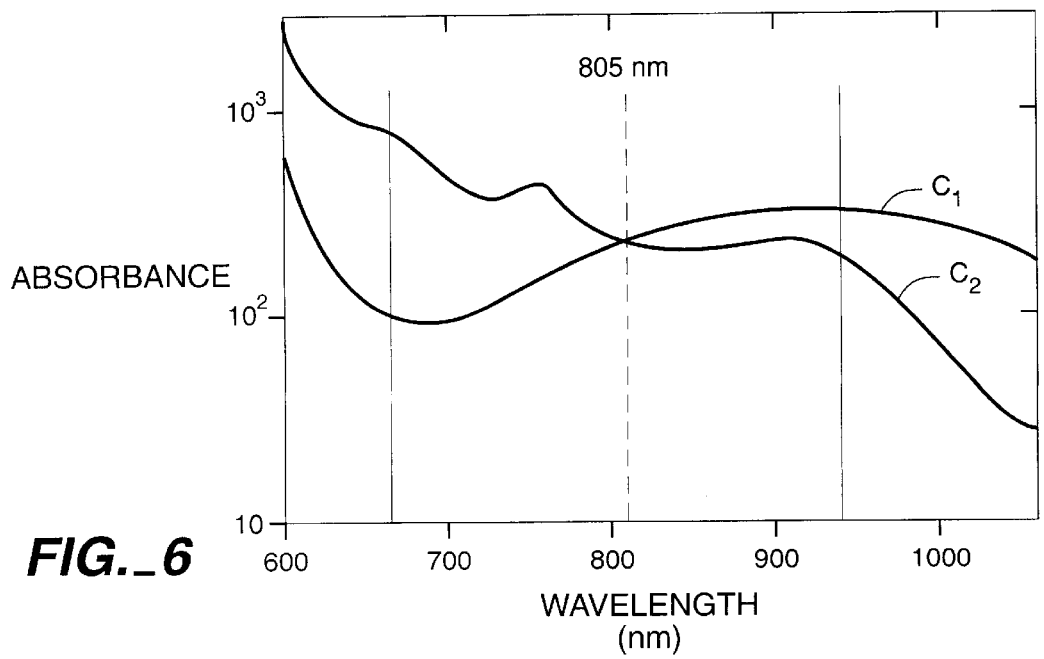
FIG._6

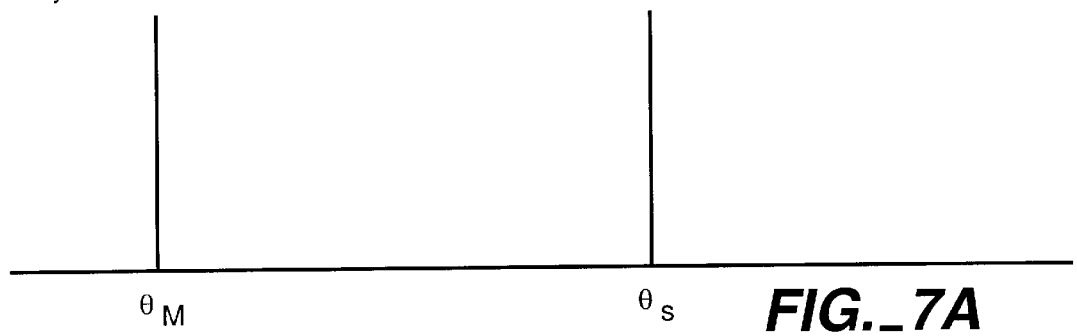
FIG._7A
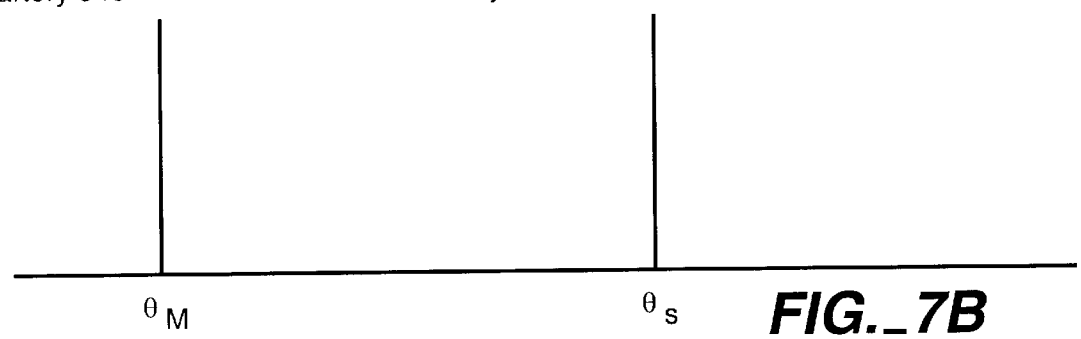
FIG._7B
FIG._8

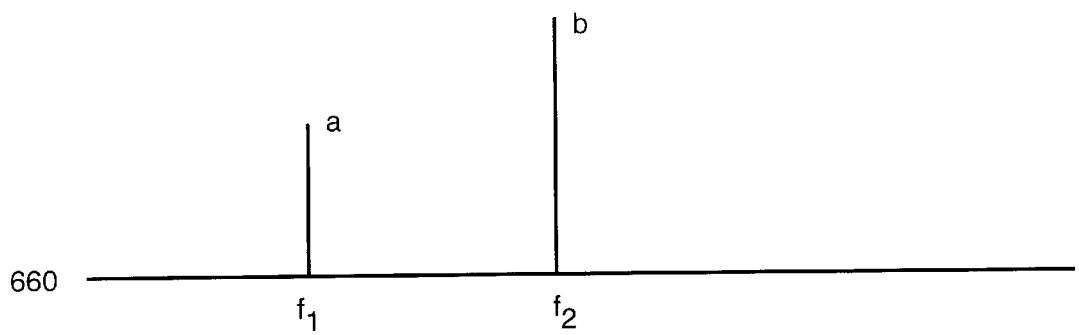
FIG._9A
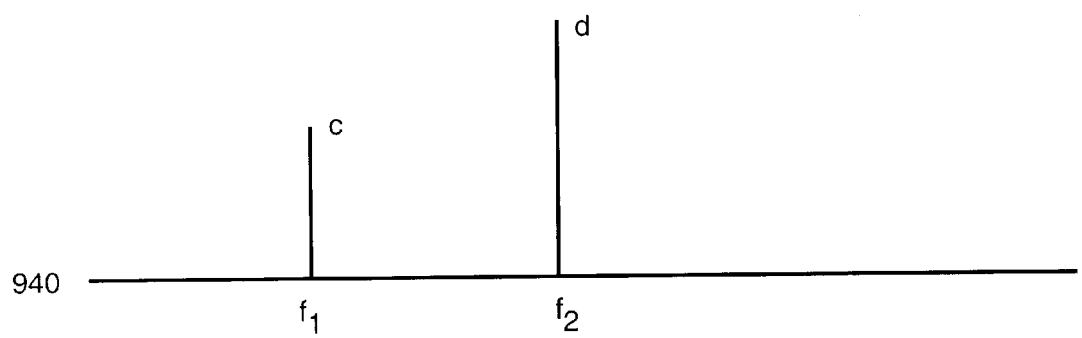
FIG._9B

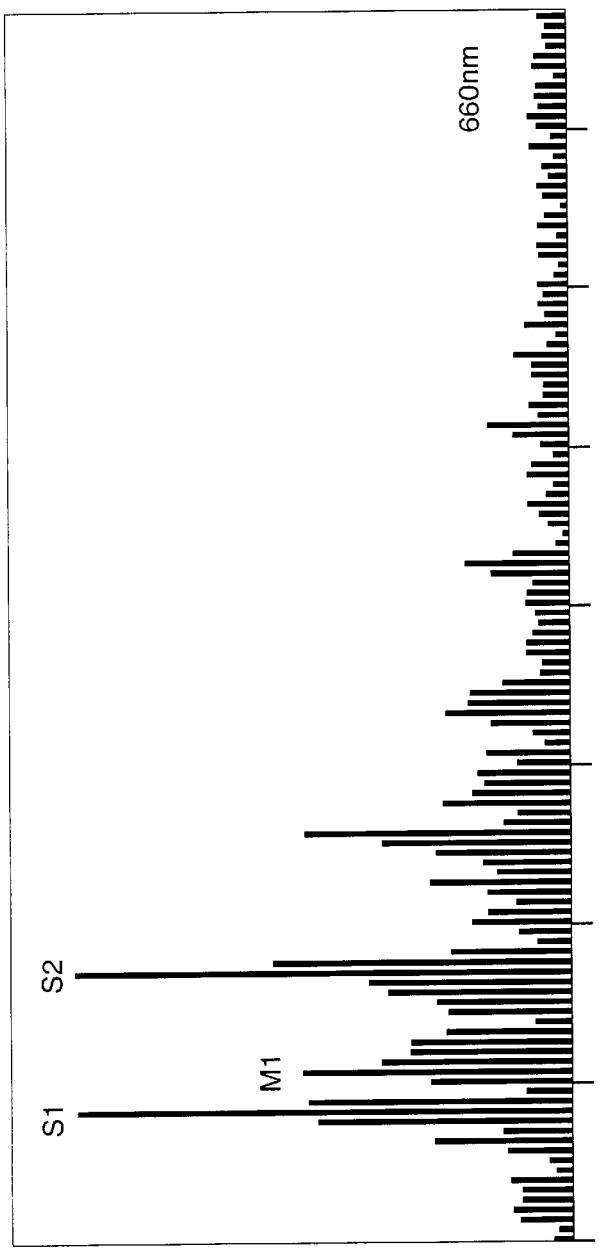
FIG._10A
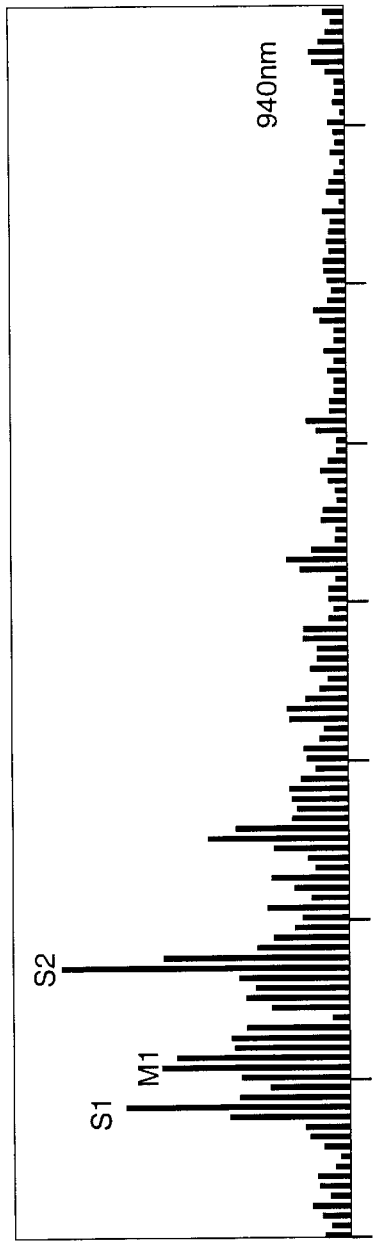
FIG._10B

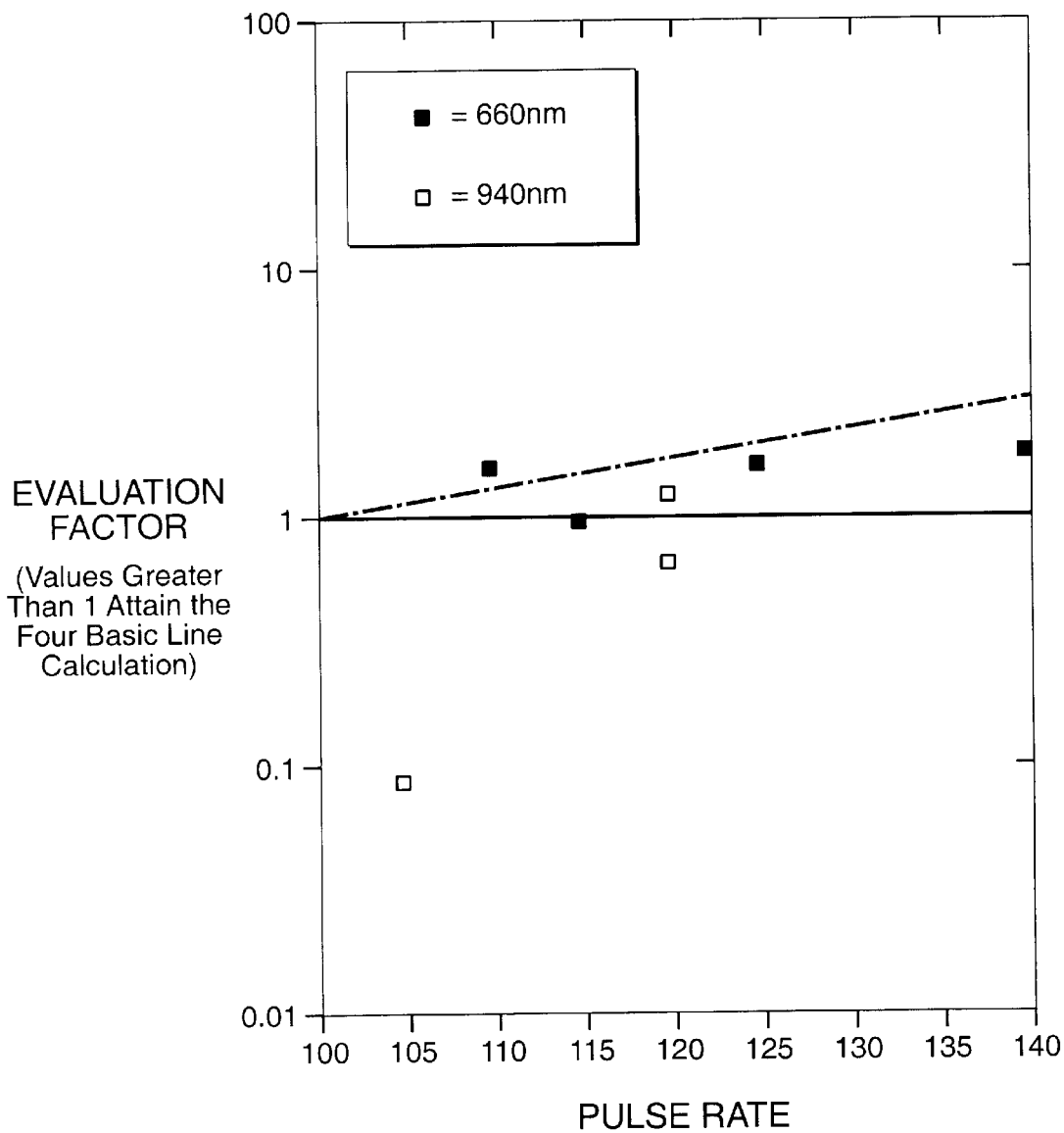
FIG._11
- Sensor Applied at the End of a Finger
- Dependence of the Stroke Pitch on the Pulse Rate During Running (Pulse Wave / First Stroke Wave)

BLOOD PULSE WAVE DETECTING APPARATUS AND MOTION INTENSITY MEASURING APPARATUS

CROSS REFERENCE TO RELATED APPLICATIONS

This application is a divisional of application Ser. No. 08/808,523 filed Feb. 28, 1997, now U.S. Pat. No. 6,022,321, which is a continuation of application Ser. No. 08/309,386 filed Sep. 20, 1994, now abandoned. Application Ser. No. 08/808,523 is incorporated by reference herein in its entirety.

BACKGROUND OF THE INVENTION

1. Field of the Invention

The present invention relates to a blood pulse wave detecting apparatus and motion intensity measuring apparatus which can perform accurate and reliable detection of the blood pulse rate, blood pulse waves, or motion intensity of a living body even if the living body is in motion.

2. Description of the Related Art

There are various types of known apparatus for detecting the blood pulse rate or blood pulse waves of a living body. However, most of these apparatus can provide accurate detection only when a living body is at rest. This is because if the living body moves, both blood pulse wave and body movement are detected, and it is impossible to extract the blood pulse wave.

The detection of the blood pulse rate or blood pulse waves of a living body is very important for control of exercise or for health care. Therefore, there is a great need for accurate blood pulse detection of a living body in motion.

In one of conventional blood pulse rate detectors as disclosed in Japanese Patent Publication No. 63-34731, when a pulse showing a deviation from an average value by an amount greater than an allowable limit is detected, the detection is cancelled so that only normal pulses can be detected. With this apparatus, extraordinary pulses which arise when a living body moves slightly for a short time can be effectively cancelled, and thus only normal pulses can be detected.

In the conventional apparatus, however, if the living body makes continuous motions, the pulse will change very often and thus the detection will be cancelled so often that accurate detection of pulses is impossible.

If the motion intensity of a living body in motion, in particular of a human body can be measured, it will be possible to advantageously control the amount of motion. However, conventional techniques cannot measure the intensity of motion.

OBJECTS OF THE INVENTION

Therefore, it is an object of the present invention to overcome the aforementioned problems.

In view of the above, it is an object of the present invention to provide a blood pulse wave detecting apparatus which can distinguish blood pulses from body motion.

It is another object of the present invention to provide a motion intensity detecting apparatus for detecting the motion intensity of a living body.

SUMMARY OF THE INVENTION

According to a first aspect of the present invention, there is provided a blood pulse wave detecting apparatus comprising: light detecting circuit for detecting the amount of light transmitted through or reflected from a living body illuminated with light having different wavelengths; and discrimination circuit for making comparison of amplitudes of frequency components associated with each wavelength, wherein the frequency components are included in a detected signal provided by the light detecting circuit, thereby discriminating a blood pulse wave of the living body from its body motion wave according to the relationships between the ratios of the amplitudes of frequency components.

According to a second aspect of the present invention, there is provided a motion intensity measuring apparatus comprising: light detecting circuit for detecting the amount of light transmitted through or reflected from a living body illuminated with light having different wavelengths; discrimination circuit for making comparison of amplitudes of frequency components associated with each wavelength wherein the frequency components are included in a detected signal provided by the light detecting means, thereby discriminating a blood pulse wave of the living body from its body motion wave according to the relationships between the ratios of the amplitudes of frequency components; and measuring circuit for making comparison of amplitudes of body motion associated with the different wavelengths, wherein the amplitudes have been discriminated by the discrimination circuit, thereby measuring the motion intensity of the living body according to the change in the ratio of the amplitudes of body motion.

According to a third aspect of the present invention, there is provided a motion intensity measuring apparatus comprising: light detecting circuit for detecting the amount of light transmitted through or reflected from a living body illuminated with light having different wavelengths; discrimination circuit for making comparison of amplitudes of frequency components associated with each wavelength wherein the frequency components are included in a detected signal provided by the light detecting circuit, thereby discriminating a blood pulse wave of the living body from its body motion wave according to the relationships between the ratios of the amplitudes of frequency components; and measuring circuit for making comparison of the amplitude of the body motion to the amplitude of the blood pulse wave, wherein the amplitudes of the body motion and blood pulse wave have been discriminated by the discrimination circuit, thereby measuring the motion intensity of the living body according to the change in the ratio between the amplitudes.

According to a fourth aspect of the present invention, there is provided a motion intensity measuring apparatus based on the second or third aspect, wherein light having a wavelength at which the absorbance of oxygen hemoglobin is equal to that of reduced hemoglobin is used as one of the light having different wavelengths, and wherein the measuring circuit employs the amplitude of a blood pulse wave included in a detected signal associated with this light as a reference value, and compares the amplitude of a blood pulse wave included in a detected signal associated with another light to the reference value, thereby measuring the motion intensity of a living body.

According to a fifth aspect of the present invention, there is provided a motion intensity measuring apparatus based on the second, third, or fourth aspect, wherein at least one of circuits including the light detecting circuits, the discrimination circuits and the measuring circuit is adapted to be supplied with electric power only when measurement is carried out.

According to a sixth aspect of the present invention, there is provided a motion intensity measuring apparatus based on the second, third, or fourth aspect, wherein at least one of circuits including the light detecting circuit, the discrimination circuit and the measuring circuit is adapted to be supplied with electric power only when measurement is carried out at measurement timing which has been set in an intermittent fashion.

According to a seventh aspect of the present invention, there is provided a motion intensity measuring apparatus based on the fifth or sixth aspect, wherein the electric power is supplied in a pulse current form.

According to an eighth aspect of the present invention, there is provided a blood pulse wave detecting apparatus comprising: light detecting circuit for detecting the amount of light transmitted through or reflected from a living body illuminated with light having different wavelengths; frequency analyzing circuit for performing frequency analysis on a detected signal provided by the light detecting circuit, for each the light having the different wavelengths; and blood pulse frequency identifying circuit for identifying the blood pulse frequency of the living body by determining which one of predefined modes the analysis result provided by the frequency analyzing circuit belongs to.

According to a ninth aspect of the present invention, there is provided a blood pulse wave detecting apparatus comprising: light detecting circuit for detecting the amount of light transmitted through or reflected from a living body illuminated with light having different wavelengths; Fourier transformation circuit for performing Fourier transformation on a detected signal provided by the light detecting circuit for each light having different wavelengths; and blood pulse frequency identifying circuit for identifying the blood pulse frequency of the living body by comparing spectra provided by the Fourier transformation circuit for the respective different wavelengths thereby determining which one of predefined modes the comparison result belongs to.

According to a tenth aspect of the present invention, there is provided a blood pulse wave detecting apparatus comprising: light detecting circuit for detecting the amount of light transmitted through or reflected from a living body illuminated with light having different wavelengths; Fourier transformation circuit for performing Fourier transformation on a detected signal provided by the light detecting circuit for each light having a different wavelength; blood pulse frequency identifying circuit for identifying the blood pulse frequency of the living body by comparing spectra provided by the Fourier transformation circuit for the respective different wavelengths, thereby determining which one of predefined modes the comparison result belongs to; and filtering circuit for passing only the frequency component identified by the blood pulse frequency identifying circuit and its harmonics included in the detected signal provided by the light detecting circuit.

According to an eleventh aspect of the present invention, there is provided a blood pulse wave detecting apparatus based on any one of the eighth through tenth aspects, further including: storage circuit for storing the identification result provided by the blood pulse frequency identifying circuit; and display circuit for displaying the content stored in the storage circuit.

According to a twelfth aspect of the present invention, there is provided a blood pulse wave detecting apparatus based on the tenth aspect, further including: waveform storing circuit for storing an output waveform provided by the filtering circuit; and display circuit for displaying the content stored in the waveform storing circuit.

According to a thirteenth aspect of the present invention, there is provided a motion intensity measuring apparatus based on any one of the second through seventh aspects, further including: motion intensity storing circuit for storing a measurement result provided by the measuring circuit; and display circuit for displaying the measurement result stored in the motion intensity storing circuit.

According to a fourteenth aspect of the present invention, there is provided a motion intensity measuring apparatus based on any one of the second through fourth aspects, wherein the light detecting circuit includes a plurality of light emitting circuits for emitting light rays having different wavelengths, and further includes a plurality of light receiving circuits for receiving reflected light associated with the light rays emitted by the respective plurality of light emitting circuits, the plurality of light emitting circuits and the plurality of light receiving circuits being arranged in the lateral direction of a finger.

According to a fifteenth aspect of the present invention, there is provided a blood pulse wave detecting apparatus based on the first, eighth, ninth, or tenth aspect, wherein the light detecting circuit includes a plurality of light emitting circuits for emitting light rays having different wavelengths, and further includes a plurality of light receiving circuits for receiving reflected light associated with the light rays emitted by the respective plurality of light emitting circuits, the plurality of light emitting circuits and the plurality of light receiving circuits being arranged in the lateral direction of a finger.

According to a sixteenth aspect of the present invention, there is provided a blood pulse wave detecting apparatus based on the first, eighth, ninth or tenth aspect, wherein at least one of the circuits including the light detecting circuit and the discrimination circuit is adapted to be supplied with electric power only when measurement is carried out.

According to a seventeenth aspect of the present invention, there is provided a blood pulse wave detecting apparatus based on the first, eighth, ninth, or tenth aspect, wherein at least one of the circuits including the light detecting circuit and the discrimination circuit is adapted to be supplied with electric power only when measurement is carried out at measurement timing which has been set in an intermittent fashion.

According to an eighteenth aspect of the present invention, there is provided a blood pulse wave detecting apparatus based on the sixteenth or seventeenth aspect, wherein the electric power is supplied in a pulse current form.

According to a nineteenth aspect of the present invention, there is provided a blood pulse wave detecting apparatus based on the first, eighth, ninth, or tenth aspect, wherein the light detecting circuit includes a plurality of light emitting circuits for emitting light rays having different wavelengths, and further includes a plurality of light receiving circuits for receiving reflected light associated with the light rays emitted by the respective plurality of light emitting circuits, the plurality of light emitting circuits and the plurality of light receiving circuits being arranged in the lateral direction of a finger.

The apparatus according to the present invention operates as follows: When a living body is illuminated with light having different wavelengths, the amount of light transmitted through or reflected from the living body depends on absorbance of oxygen hemoglobin included in arterial blood and also depends on reduced hemoglobin included in venous blood. Furthermore, the absorbances of both oxygen hemoglobin and reduced hemoglobin depend on wavelength of light in different fashions. When a living body is in motion, the body motion is superimposed on both arterial blood and venous blood. Therefore, the amount of light detected by the light detecting circuit is influenced by the absorbance, which is dependent on the wavelength, as well as the body motion. Thus, if amplitudes of frequency components included in a signal detected by the light detecting circuit are compared to one another for each wavelength, the blood pulse wave can be discriminated from the body motion wave according to the relationships between the ratios of amplitudes (the first aspect).

The absorbance of reduced hemoglobin varies depending on its oxygen content, that is, on the motion intensity. Therefore, if the body motion wave is discriminated from the blood pulse wave, and furthermore the amplitudes of body motion waves are compared between different wavelengths, then the motion intensity of a living body can be measured according to the change in the ratio of the amplitudes (the second aspect). The motion intensity can also be measured according to the change in the ratio of the amplitude of the body motion wave to the amplitude of the blood pulse wave (the third aspect).

If light having a wavelength at which the absorbance of oxygen hemoglobin is equal to that of reduced hemoglobin is employed as one of measuring light rays, then the amount of received light associated with this light can be used as a reference value (the fourth aspect).

The blood pulse wave can also be identified by performing frequency analysis on a signal detected by the light detecting circuit and determining which one of predefined modes the analysis result belongs to (the fifth aspect).

The blood pulse frequency can be determined by performing Fourier transformation, which is one of way to perform frequency analysis, and comparing the resultant spectra (the sixth aspect).

The blood pulse wave can be detected by using filter circuit which passes only a specific frequency component and its harmonics (the seventh aspect).

Other objects and attainments together with a fuller understanding of the invention will become apparent and appreciated by referring to the following description and claims taken in conjunction with the accompanying drawings.

BRIEF DESCRIPTION OF THE DRAWINGS

In the drawings wherein like reference symbols refer to like parts

FIG. 1 is a block diagram illustrating the configuration of an embodiment of the present invention;

FIGS. 2A and 2B are diagrams illustrating sensors for use in the embodiment, wherein the sensors are attached to a finger;

FIG. 3 is a representation of the "Lambert's" law;

FIG. 4 is a representation of an absorbance distribution of a human blood vessel illuminated with light;

FIG. 5 is a graph illustrating the change in blood pulses as a function of distance from a heart from the left ventricle to the large vein;

FIG. 6 is a graph illustrating absorbance characteristics of oxygen hemoglobin and reduced hemoglobin;

FIGS. 7A and 7B are diagrams illustrating amplitudes of detected signal components corresponding to blood pulses and body motion, respectively, for both cases where the detection is carried out with light having wavelengths 660 nm and 940 nm;

FIG. 8 is a diagram illustrating the relationships of absorbance between arterial blood and venous blood for both cases where the detection is carried out with light having wavelengths 660 nm and 940 nm;

FIGS. 9A and 9B are diagrams illustrating the method of determining the correspondence between two frequency components detected with two light rays having wavelengths of 660 nm, 940 nm and their origins, that is, blood pulses and body motion;

FIGS. 10A and 10B are graphs illustrating frequency spectra of signals detected with light having wavelengths of 660 nm and 940 nm; and FIG. 11 is a diagram illustrating an example of an actual measurement of the change in the ratio of the amplitude associated with frequency $\theta_S$ to the amplitude associated with frequency $\theta_M$ wherein the measurement was carried out using light with a wavelength of 660 nm.

DESCRIPTION OF THE PREFERRED EMBODIMENTS

A: Detection Principle of the Invention

In the present invention, pulse waves and motion intensity is detected according to the following principle:

(a) The Principle of Detecting Pulses via Light

First, the principle of detection of blood pulses via light will be described. When a thin film is illuminated with light, the ratio of the intensity of transmitted light to that of incident light decreases depending on the density of matter and on the optical length. This fact is known as the "Lambert's" law.

According to this law, the density of matter can be determined as follows: As shown in FIG. 3A, if the density of matter M is represented by C, a small optical length by $\Delta L$, the amount of incident light by $I_{in}$, the absorption factor of the matter M by k, then the following equation holds.

$$I_{out}/I_{in} = 1 - kC \Delta L \quad (1)$$

If the optical path is increased by a factor of 5 as shown in FIG. 3B, equation 1 becomes:

$$I_{out}/I_{in} = (1 - kC\Delta L)^5 \quad (2)$$

In the first case in FIG. 3, for example, when the amount of incident light $I_{in}$ is 10, if the amount of transmitted light is 9, then in the second case of FIG. 3B, when the amount of incident light $I_{in}$ is 10, the amount of transmitted light will be $10 \times 0.9^5$, or $I_{out}/I_{in} = 0.9^5$.

The relationship between the amount of incident light and the amount of transmitted light for arbitrary distance L can be obtained by integrating equation 1, thus:

$$log(I_{out}/I_{in}) = (-kCL) \quad (3)$$

Equation 3 can be rewritten as:

$$I_{out} = I_{in} \times exp(-kCL\_) \quad (4)$$

As can be seen from the above equation, if the amount of incident light $I_{in}$, the absorption factor k, and the optical length L are all maintained constant, then it is possible to measure the change in density of matter M by detecting the amount of transmitted light $I_{out}$.

Instead of detecting the amount of transmitted light, it is also possible to measure the change in density by detecting the amount of the light reflected from the matter M according to the same principle.

When a human blood vessel is illuminated with external light, the distribution of the absorption factor will be such as that shown in FIG. 4. In the figure, $I_2$ represents the absorption caused by tissue, $I_3$ represents the absorption caused by venous blood, and $I_4$ represents the absorption caused by arterial blood.

Because the density of tissue does not change, the absorption $I_2$ caused by tissue is constant. The absorption $I_3$ by venous blood is also constant. This is because there in no pulsation in venous blood and therefore there is no change in its density. This can be seen apparently from FIG. 5, which shows the decay of pulsation of blood sent from a heart with distance from the heart. When blood reaches a vein, pulsation no longer occurs.

On the other hand, the absorption $I_4$ by arterial blood shows a change corresponding to the change in density induced by pulses. This means that pulses can be detected by illuminating a blood vessel with light and detecting the change in the amount of reflected or transmitted light. The above-described detection principle is also disclosed in Japanese Patent Laid-Open No. 2-44534.

If a human body is in motion, the body movement influences the flow of blood through vessels including veins. As a result, the flow of venous blood becomes dynamic. This produces a change in light absorption of venous blood. Similarly, when arms or legs are in swing motion, vibrations of tissue also produce a change in its light absorption. Therefore, when a human body is in motion, simple detection of the amount of light reflected from or transmitted through a vessel cannot effectively detect pulses.

(b) The Principle of Detecting Pulse Waves of a Living Body in Motion

The principle of detecting the pulse rate of a living body in motion will be described below.

Curves C1 and C2 in FIG. 6 respectively represent the absorption spectrum of hemoglobin (hemoglobin combined with a sufficient amount of oxygen, which will be referred to as oxygen hemoglobin hereinafter) provided by a heart, and the absorption spectrum of hemoglobin (reduced hemoglobin) returning to a heart through a vein, oxygen of which has been consumed by a body. As shown in FIG. 6, the absorbance depends on the wavelength of light. The oxygen hemoglobin shows strong absorption of light in an infrared range (with a peak at 940 nm), and the reduced hemoglobin shows strong absorption of light in a red range (with peak at 660 nm). Both types hemoglobin have similar absorbance for light near 805 nm.

The difference in absorption characteristics between two types of hemoglobin results from the difference in the amount of oxygen. The absorption spectrum changes from curve C1 to C2 with the consumption of oxygen.

When a human body is in motion, it consumes a greater amount of oxygen than when it is at rest. Therefore, the absorption characteristic of reduced hemoglobin varies depending on the amount of consumed oxygen. In contrast, it is known that oxygen content combined with hemoglobin in arterial blood (or oxygen saturation ratio of arterial blood) is maintained constant regardless of the motion intensity. Therefore, if absorption is measured for different wavelengths, the motion intensity of a living body can be determined by comparing the results obtained at different wavelengths. In this technique, if the measurement is carried out for example at 940 nm and 660 nm, it is possible to achieve emphasized detection of motion intensity.

When a living body is in motion, because the body movement influences the flow of blood, the light transmitted through or reflected from a vessel includes pulses produced by the body movement superimposed on normal pulses. This body movement components should be distinguished. Otherwise, it would be impossible to detect either normal pulses or motion intensity. This point will be further discussed below.

The detection of pulse waves of a living body at rest by means of light can be represented by the following equation:

The amount of received light=The amount of emitted light−The amount of light absorbed by tissue−$K_{artery}$·(Artery DC component+Pulse amplitude·$F(\theta_M)$)−$K_{vein}$·Vein level (5)

where $K_{artery}$ is the absorbance of arterial blood, $K_{vein}$ is the absorbance of venous blood, artery DC component is the DC component (constant component) of arterial blood, and vein level is the flow rate of venous blood (which has no pulse component as described above). Furthermore, $F(\theta_M)$ is the AC component of arterial blood, or a periodic function representing an amplitude (pulse amplitude) of the amount of hemoglobin which varies in an AC fashion at frequency $\theta_M$.

When the living body is in motion, pulse components induced by the body movement are superimposed on both artery and vein. The amount of light which is received when the living body is in motion can be represented by adding these components to equation 5. For example, when an arm is in swing motion, the following equation holds:

The amount of received light=The amount of emitted light−The amount of light absorbed by tissue−$K_{artery}$·(Artery DC component+Pulse amplitude·$F(\theta_M)$+Arm amplitude·$F'(\theta_S)$)−$K_{vein}$·(Vein level+Arm amplitude·$F'(\theta_S)$) (6)

In this equation, arm amplitude·$F'(\theta_S)$ is a periodic function having an amplitude (arm amplitude) of an AC component corresponding to the variation in the amount of hemoglobin induced by strokes of an arm and having a frequency of $\theta_S$.

The amount of received light represented by equation 6 can be further modified as the following equations for the case where the detection is done at two different wavelengths (660 nm and 940 nm in this example).

The amount of received light (660)=The amount of emitted light (660)−The amount of light absorbed by tissue (660)−$K_{artery660}$·(Artery DC component)+Pulse amplitude·$F(\theta_M)$+Arm amplitude·$F'(\theta_S)$)−$K_{vein660}$·(Vein level+Arm amplitude·$F'(\theta_S)$) (7)

The amount of received light (940)=The amount of emitted light (940)−The amount of light absorbed by tissue (940)−$K_{artery940}$·(Artery DC component+Pulse amplitude·$F(\theta_M)$+Arm amplitude·$F'(\theta_S)$)−$K_{vein940}$·(Vein level+Arm amplitude·$F'(\theta_S)$)(8)

In the above equations 7 and 8, subscripts 660 and 940 represent wavelengths at which the detection is done, and the terms or coefficients having subscripts represent the values at the corresponding wavelengths.

The amount of light given by equation 7 or 8, which will be referred to as a "received signal" hereinafter, is a periodic function represented in the time domain. If each received signal is subjected to the Fourier transformation, amplitudes of frequency components included in each received signal can be detected. In FIG. 7A, for example, the amplitude corresponding to $K_{artery660}$·Pulse amplitude, or the amplitude of the frequency component associated with pulses of arterial blood, is detected at frequency $\theta_M$ for the wavelength of 660 nm, and the amplitude corresponding to ($K_{artery660}+K_{vein660}$)Arm amplitude or the amplitude of the frequency component associated with strokes of an arm superimposed on both vein and artery is detected at frequency $\theta_S$. As shown in FIG. 7B, similar amplitudes are also detected at the same frequencies in the case of the wavelength of 940 nm.

If the absorbance characteristics shown in FIG. 6 are taken into account, the relationships in absorbance between arterial blood and venous blood for the respective wavelengths are such as those shown in FIG. 8, are represented by the following inequalities:

$$K_{artery660} < K_{vein660}, K_{artery940} > K_{vein940} \qquad (9)$$

For example, as shown in FIG. 9, when amplitudes of components at frequencies $f_1$ and $f_2$ are a and b, respectively, for the wavelength of 660 nm, and b and c, respectively, for the wavelength of 940 nm, if (a/b)<(c/d) or (c/d)>(d/b), then it is concluded that $f_1$ is the frequency corresponding to arterial blood pulses, and $f_2$ is the frequency corresponding to arm swinging.

Once the frequency corresponding to arterial blood pulses has been detected, the pulse rate can be determined by converting the frequency to a number of pulses per minute. In this way, the pulse rate of a living body in motion can be detected.

FIG. 10 illustrates one example of experimental results, wherein FIGS. 10A and 10B frequency spectra of signals detected for wavelengths of 660 nm and 940 nm, respectively. In this experiment, a man under examination swung his arms at a constant rate in synchronism with a metronome as in running, and the pulses were also measured by an electrocardiograph for verification. In FIGS. 10A and 10B, S1 denotes a fundamental frequency of arm strokes (body motion), S2 denotes the second-order harmonic of the arm strokes, and M1 denotes the fundamental frequency of blood pulses (i.e., the pulse rate).

If the ratio of M1 to S1 is compared with the ratio shown in FIG. 10A and the ratio shown in FIG. 10B, it is concluded from the above relationships that M1 represents pulses. The pulse ratio obtained in this way shows good agreement with that obtained by the electrocardiograph.

(c) The Principle of Detecting Motion Intensity

If the arterial blood pulse frequency and the body motion frequency are discriminated, the motion intensity of a living body can be detected by comparing the amplitudes of these frequency components. In FIGS. 7A and 7B, the amplitude of the frequency component $\theta_S$ representing the body motion (strokes) depends on the light absorbance of arterial and venous blood. The absorbance of arterial blood is constant regardless of the change in motion intensity, while the absorbance of venous blood varies depending on the motion intensity (the amount of oxygen consumption). As a result, the motion intensity can be determined as follows:

(1) The amplitude at frequency $\theta_S$ associated with the wavelength of 660 nm or 940 nm is sampled in a proper manner. The change in motion intensity of a living body in motion can be detected from the change in the sampled value which reflects the motion intensity.

(2) If the comparison of the ratio of the amplitude at frequency $\theta_S$ to the amplitude at frequency $\theta_M$ is made between wavelengths of 660 nm and 940 nm, the ratio reflects the motion intensity because the amplitude at frequency $\theta_M$ is independent of the motion intensity. From the change in this ratio, therefore, it is possible to detect the change in motion intensity of a living body. If the relationship between the above ratio and the motion intensity has been examined and stored in memory, the motion intensity can be determined by referring to the information stored in the memory.

FIG. 11 illustrates the data actually measured with respect to the ratio of the amplitude at frequency $\theta_S$ to the amplitude at frequency $\theta_M$ (corresponding to the ratio a/b in FIG. 9) for the wavelength of 660 nm. In this measurement, a man under examination was forced to be in continuous motion, and the amplitudes at various frequencies were measured. The ratios of amplitudes are plotted as a function of the pulse rate. As represented by the alternate long and short dash line in FIG. 11, the plotted points show a tendency to increase with the pulse rate. An increase in pulse rate can be regarded as an increase in motion intensity. An increase in motion intensity results in an increase in oxygen consumption of blood, and thus results in an increase in light absorbance. As a result, the amplitude at frequency $\theta_S$ (which corresponds to "b" in FIG. 9) decreases with increasing motion intensity, and thus the ratio a/b increases. Therefore, the motion intensity can be detected from the change in ratio a/b.

(3) Light having a wavelength of about 805 nm is used to give a reference value of the amount received light. At this wavelength, both oxygen hemoglobin and reduced hemoglobin have constant absorbance, as shown in FIG. 6. Therefore, the received signal associated with light having such a wavelength can be used to give a reference value for comparing with the amplitude of a component having a frequency of $\theta_S$ included in a received signal associated with light having another wavelength. From the change of this ratio, the motion intensity can be detected.

(d) The Principle of Detecting the Pulse Waveform of a Living Body in Motion

If the frequency reflecting artery blood pulses can be distinguished in the above-described manner, it is possible to detect a pulse waveform by using a filter which can pass this frequency and its harmonics.

A pulse wave includes a fundamental wave and various orders of harmonics. If these components are extracted using a filter which can pass these components but which cannot pass other frequency components, the pulse wave associated with a living body in motion can be detected.

B: The Construction of Embodiments

With reference to the accompanying drawings, the embodiments of this invention will be described below.

FIG. 1 is a block diagram illustrating the construction of one embodiment of this invention. In this figure, photosensors 1 and 2 are of the photo-coupler type for wavelengths 660 nm and 940 nm, respectively. As shown in FIG. 2A, these sensors 1 and 2 are disposed in an appropriate cap. The cap is adapted to be attached to the end portion of a finger in such a manner that sensors 1 and 2 are arranged in the longitudinal direction of the finger. Otherwise, the cap may be adapted such that sensors 1 and 2 are arranged in the lateral direction of a finger when the cap is attached to the finger.

The light beams emitted by the sensors 1 and 2 are reflected from blood vessels or tissue, and detected by photo-sensing elements of sensors 1 and 2. As shown in FIG. 1, the detected signals are applied as signals Sa and Sb, respectively, to a fast Fourier transformation circuit 3. The fast Fourier transformation circuit 3 performs the Fourier transformation on signals Sa and Sb, and provides frequency spectra associated with these signals. The frequency spectra provided by fast Fourier transformation circuit 3 are applied to a comparator 4. Comparator 4 stores the frequency spectra temporarily, and compares the magnitudes of major lines included in the spectra with one another. For example, the magnitudes of S1 and M1 shown in FIG. 10A are compared. Similarly, the magnitudes of S1 and M1 shown in FIG. 10B are compared. The comparison results are supplied to a decision circuit 5. Referring to comparison result patterns previously stored, decision circuit 5 determines which frequency corresponds to pulses and which one corresponds to body motion. As described above, if amplitudes a, b, c, and d of frequency components $f_1$ and $f_2$ shown in FIG. 9 satisfy the relationship (a/b)<(c/d) or (c/a)>(d/b), then it is decided that frequency $f_1$ corresponds to arterial blood pulses, and that frequency $f_2$ corresponds to arm strokes. According to the decision made by the decision circuit 5, a display unit 6 including a liquid crystal display elements or the like converts the frequency fc, which has been considered to correspond to the pulse rate, into a frequency per minute, and displays it on display the elements.

According to the comparison results provided by comparator 4, decision circuit 5 detects the change in motion intensity from the ratio of the amplitude at frequency S1 to the amplitude at frequency at M1 associated with the wavelength of 660 nm or 940 nm, and outputs a signal representing the detection result to display unit 6. The display unit 6 displays the change of motion intensity in a numerical or graphic fashion.

An active filter 10 extracts the frequency fc considered to correspond to blood pulses and its harmonics (for example, up to fifth- or sixth-order harmonics) from the output signal Sa or Sb outputted by sensor 1 or 2. Therefore, the output signal of the active filter 10 is a pure pulse wave signal containing no stroke components (body motion components).

A measuring circuit 11 performs various kinds of measurement on the basis of the pulse wave signal provided by active filter 10. For example, experiments have revealed that the ratio of the amplitude of the second-order harmonic to the amplitude of the third-order harmonic reflects the stress. It is also known that the mental and physical status can be measured from characteristic features of pulse waves. Thus, measuring circuit 11 analyzes the pulse waves according to predetermined analytic methods, and outputs a signal representing the result to display unit 6. Display unit 6 displays the measured result according to the output signal of the measuring circuit 11.

C: The Operation of the Embodiment

First, a person to be examined attaches the cap shown in FIG. 2 to one of his or her fingers, and then exercises (runs, for example). Signals Sa and Sb including a blood pulse wave and body motion components superposed on it are obtained. These signals Sa and Sb are subjected to Fourier transformation in the fast Fourier transformation circuit 3. Then, amplitudes of major frequency components are compared to one another by comparator 4. According to the comparison result, decision circuit 5 discriminates the pulse wave and the body motion. Display unit 6 displays a pulse rate corresponding to the fundamental frequency of the pulse wave. Display unit 6 stores the pulse rate, and continues displaying this stored value until the pulse rate has been updated. Display unit 6 also displays the change of motion intensity detected by decision circuit 5. Thus, during the exercise, it is possible to observe the change in motion intensity of the person under examination.

Active filter 10 extracts only pulse wave components and outputs them to the measuring circuit 11, which in turn performs measurement. In this way, the pulse wave of the person in motion is detected, and his or her mental and physical status is detected from the pulse waveform. The detected results are displayed on display unit 6 so that the mental and physical status (stress, for example) can be observed during his or her exercising.

In the above example, comparator 4 makes comparison of amplitudes between the fundamental wave of a pulse wave and the fundamental wave of body motion. However, the invention is not limited only to such comparison. Comparator 4 may also compare, for example, the fundamental wave of a pulse wave to the second-order harmonic of body motion, or compare the second-order harmonic of the pulse wave to the fundamental wave of body motion. Basically, any waves which can be clearly discriminated can be designated for use in comparison. In some cases, body motion of a person under examination does not have periodicity. In this case, since major frequency components obtained by the Fourier transformation all result from blood pulses, it is much easier to discriminate the pulse wave. In comparator 4 of this embodiment, when the output signal of fast Fourier transformation circuit 3 contains only one fundamental wave and its harmonics, it is concluded that only blood pulse waves are detected, and its fundamental wave is regarded as blood pulses.

D: Modifications

The above-described embodiment can be modified as follows:

(1) In the above embodiment, sensors are attached to the end portion of a finger to detect pulse waves at the end of the finger. Alternatively, the sensors may also be attached in such a manner that pulse waves at the root portion of a finger can be detected. Furthermore, the sensors may also be attached to detect blood pulses at a radius or at an ear. In addition to those described above, the sensors may be attached to an arbitrary portion as long as an artery and vein passing through that portion can be illuminated with light.

(2) In the above embodiment, sensors are attached with a cap (as in FIG. 1). However, the sensors may also be attached in a different manner. For example, a glove, band, tape, or the like may be used to attach the sensors to a portion for detected.

(3) In the above embodiment, the Fourier transformation is utilized to perform frequency analysis on a sensed signal. Alternatively, discrete Fourier transformation or maximum entropy scheme may be employed. Basically, any method, which can extract frequency components included in a sensed signal and can compare amplitudes of these components to one another, can be employed.

(4) In the above embodiment, light beams having wavelengths of 660 nm and 940 nm are used for measurement. However, the wavelength is not limited only to those. Arbitrary wavelengths which lead to a difference in absorbance between oxygen hemoglobin and reduced hemoglobin may be employed.

(5) Furthermore, a light ray having a wavelength of 805 nm can be used as a reference light ray for measurement. At this wavelength, as shown in FIG. 6, there is no difference in absorbance between oxygen hemoglobin and reduced hemoglobin. Therefore, the received signal associated with the light having this wavelength can be used to give a reference value for comparing with the amplitude of a component having a frequency of $\theta_S$ included in a received signal associated with light having another wavelength. From the change of this ratio, the absolute value of the motion intensity can be detected.

(6) According to the above embodiment, it is possible to detect the frequency of body motion. Therefore, arm strokes during walking or running can be detected. Because the arm strokes correspond to the pitch of walking or running, the detection of body motion frequency allows the detection of the sum of step number. That is, the embodiment of this invention can also be used as a pedometer.

(7) Measuring circuit 11 may be adapted to include a pulse wave memory to store pulse waves outputted by active filter 10, and pulse waves stored in the pulse wave memory may be displayed on the display unit 6. This arrangement allows visual recognition of the pulse wave form. This facilitates a grasp of the mental and physical status of a person under examination.

(8) There may be provided a motion intensity memory for temporarily storing the motion intensity detected by decision circuit 5, and the motion intensity (or the change in motion intensity) stored in the motion intensity memory may be displayed on display unit 6. This arrangement allows visual recognition of the motion intensity (or the change in motion intensity). This facilitates a grasp of more detailed mental and physical status of a person under examination.

(9) There may be provided a switch for performing on-off control of electric power, thereby supplying the power to the entire circuit shown in FIG. 1 or a specific part of the circuit only when measurement is carried out.

Furthermore, the above embodiment can be modified such that measurement is carried out at predetermined timing. In other words, electric power is intermittently supplied to the entire of the circuit or a specific part of the circuit only at the predetermined timing for the measurement. In this case, the measurement timing can be set using a timer implemented in a hardware circuit or can be programmed in a microcomputer.

Furthermore, in either case where the electric power is supplied in on-off switching fashion or intermittent fashion, the power may be supplied in the form of a pulse current, thereby achieving a great reduction in power consumption.

According to the present invention, as described above, it is possible to perform accurate and reliable detection of the pulse ratio or the pulse wave of a living body which is even in continuous motion. Furthermore, it is also possible to detect the motion intensity during the motion of a living body.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

What is claimed is:

1. A motion intensity measuring apparatus, comprising:
   light detecting means for detecting the amount of light transmitted through or reflected from a living body illuminated with light having different wavelengths;
   discrimination means for making comparison of amplitudes of frequency components associated with each said wavelength wherein said frequency components are included in a detected signal provided by said light detecting means, thereby discriminating a blood pulse wave of said living body from its body motion wave according to the relationships between the ratios of said amplitudes of frequency components; and
   measuring means for making comparison of amplitudes of body motion associated with said different wavelengths wherein said amplitudes have been discriminated by said discrimination means, thereby measuring the motion intensity of said living body according to the change in the ratio of said amplitudes of body motion.

2. A motion intensity measuring apparatus according to claim 1, wherein light having such a wavelength at which the absorbance of oxygen hemoglobin is equal to that of reduced hemoglobin is used as one of said light having different wavelengths, and wherein said measuring means employs the amplitude of a blood pulse wave included in a detected signal associated with this light as a reference value, and compares the amplitude of a blood pulse wave included in a detected signal associated with another light to said reference value, thereby measuring said motion intensity of a living body.

3. A motion intensity measuring apparatus according to claim 1, wherein at least one of means including said light detecting means, said discrimination means and said measuring means is adapted to be supplied with electric power only when measurement is carried out.

4. A motion intensity measuring apparatus according to claim 3, wherein said electric power is supplied in a pulse current form.

5. A motion intensity measuring apparatus according to claim 1, wherein at least one of means including said light detecting means, said discrimination means and said measuring means is adapted to be supplied with electric power only when measurement is carried out at measurement timing which has been set in an intermittent fashion.

6. A motion intensity measuring apparatus according to claim 1, further including:
   motion intensity storing means for storing a measurement result provided by said measuring means; and
   display means for displaying the measurement result stored in said motion intensity storing means.

7. A motion intensity measuring apparatus according to claim 1, wherein said light detecting means includes a plurality of light emitting means for emitting light rays having different wavelengths, and further includes a plurality of light receiving means for receiving reflected light associated with the light rays emitted by respective said plurality of light emitting means, said plurality of light emitting means and said plurality of light receiving means being arranged in the lateral direction of a finger.

8. A motion intensity measuring apparatus, comprising:
   light detecting means for detecting the amount of light transmitted through or reflected from a living body illuminated with light having different wavelengths;
   discrimination means for making comparison of amplitudes of frequency components associated with each said wavelength wherein said frequency components are included in a detected signal provided by said light detecting means, thereby discriminating a blood pulse wave of said living body from its body motion wave according to the relationships between the ratios of said amplitudes of frequency components; and
   measuring means for making comparison of the amplitude of the body motion to the amplitude of the blood pulse wave wherein the amplitudes of the body motion and blood pulse wave have been discriminated by said discrimination means, thereby measuring the motion intensity of said living body according to the change in the ratio between the amplitudes.

* * * * *